(12) United States Patent
Bertozzi et al.

(10) Patent No.: US 6,713,274 B2
(45) Date of Patent: Mar. 30, 2004

(54) METHOD FOR IDENTIFYING MODULATORS OF SULFOTRANSFERASE ACTIVITY

(75) Inventors: Carolyn Bertozzi, Berkeley, CA (US); Dawn Verdugo, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 9 days.

(21) Appl. No.: 10/145,648

(22) Filed: May 13, 2002

(65) Prior Publication Data

US 2003/0211562 A1 Nov. 13, 2003

(51) Int. Cl.$^7$ .................. C12G 1/48; C12G 1/00; G01N 33/53
(52) U.S. Cl. ............... 435/15; 435/4; 435/968
(58) Field of Search .............. 435/15, 4, 968, 435/975

(56) References Cited

U.S. PATENT DOCUMENTS

| 6,365,365 B1 | 4/2002 | Bistrup et al. ............. 435/15 |
| 2003/0109501 A1 * | 6/2003 | Yang et al. ............... 514/102 |

OTHER PUBLICATIONS

Kusche et al, J. Biological Chemistry, vol. 266, No. 12, p 7400–7409, (Apr. 26, 1991).*
Armstrong, et al. "Sulfotransferases as targets for therapeutic intervention", *Curr. Opin. Drug Disc. Dev.*, (2000) vol. 3: 502–515.
Burkart, et al. "A continuous assay for the spectrophotometric analysis sulfotransferases using aryl sulfotransferase IV", *Anal. Biochem.*, (1999) vol. 274: 131–137.
Cook, et al. "Differential carbohydrate recognition of two GlcNAc–6–sulfotransferases with possible roles in L–selectin ligand biosynthesis", *J. Am. Chem. Soc.*, (2000) vol. 122: 8612–8622.
Hemmerich, et al. "Carbohydrate sulfotransferases in lymphocyte homing", *Glycobiol.*, (2000) vol. 10(9): 849–856.
Hooper, et al. "Sulfotransferase and glycosyltransferase analyses using a 96–well filtration plate", *Anal. Biochem.*, (1993) vol. 212: 128–133.
Kehoe, et al. "Tyrosylprotein sulfotransferase inhibitors generated by combinational target–guided ligand assembly", *Bio. Org. Med. Chem. Lett.*, (2002) vol. 12: 329–332.
Mandon, et al. "A monomeric protein in the golgi membrane catalyzes both N–deacetylation and N–sulfation of heparan sulfate", *J. Biol. Chem.*, (1994) vol. 269: 11729–11733.
Sueyoshi, et al. "A role of Lys$^{614}$ in the sulfotransferase activity of human heparan sulfate N–deacetylation/N–sulfation", *FEBS Lett.*, (1998) vol. 433: 211–214.
Sugahara, et al. "Paper disk assay for glycosaminoglycan sulfotransferases", *Anal. Biochem.*, (1987) vol. 166: 404–412.

* cited by examiner

*Primary Examiner*—Louise N. Leary
(74) *Attorney, Agent, or Firm*—Paula A. Borden; Bozicevic, Field & Francis, LLP (57) ABSTRACT

The instant invention provides methods for identifying agents that modulate an enzymatic activity of a carbohydrate sulfotransferase. The methods generally involve contacting the sulfotransferase, in a reaction solution, with a sulfate donor, a test agent, and a polymeric sulfate acceptor that is readily separated from the reaction solution. Determination of an effect of the test agent on the sulfotransferase is by detecting the amount of sulfate in the polymeric sulfate acceptor that has been separated from the reaction solution. The invention further provides kits for use in carrying out the subject methods.

17 Claims, 5 Drawing Sheets

METHOD FOR IDENTIFYING MODULATORS OF SULFOTRANSFERASE ACTIVITY

STATEMENT REGARDING FEDERALLY SPONSORED RESEARCH

The U.S. government may have certain rights in this invention, pursuant to grant nos. GM08352 and GM59907 awarded by the National Institutes of Health.

FIELD OF THE INVENTION

This invention is in the field of sulfotransferase enzymes, and in particular assay methods for identifying agents that modulate sulfotransferase activity.

BACKGROUND OF THE INVENTION

Sulfation of biomolecules is now appreciated as a major regulatory modification that affects interactions in the extracellular space. The sulfotransferases (STs) are a family of enzymes that catalyzes the sulfation of biomolecules. Many STs act on glycoproteins in the Golgi compartment. Dozens of STs have been discovered, and in some cases the epitopes they generate have been linked to disease processes. For example, specific carbohydrate sulfates govern growth factor binding and activation, and leukocyte adhesion during inflammation. Tyrosine sulfation is a prerequisite for HIV-1 binding to host cell co-receptors in addition to other cell adhesion events. These examples have piqued the interests of both biologists and medicinal chemists, as STs are emerging as attractive therapeutic targets.

There has been some progress in the development of relatively efficient assays for individual carbohydrate STs. A traditional architecture involves radiolabel transfer from $^{35}$S-labeled 3'-phosphoadenosine 5'-phosphosulfate (PAPS) to a carbohydrate substrate bearing a hydrophobic tail for capture on reversed-phase cartridges. While this approach can be adapted to 96-well format, it requires several labor-intensive washing and elution steps in order to purify the sulfated product before quantitation by liquid scintillation. Biotinylated substrates have been used for sulfotransferase assays, wherein capture with immobilized avidin separates the $^{35}$S-labeled products from unreacted $^{35}$S-labeled PAPS. Fewer washing steps are required, but microtiter plate-based systems that immobilize avidin are fairly expensive, particularly for high-throughput screens. Wong and co-workers reported an enzyme-coupled continuous spectrophotometric assay that could in principle be applied to any sulfotransferase. While ideal for kinetic assays, the presence of a second enzyme, in this case an aryl sulfotransferase, might complicate ST-targeted inhibitor screens.

Therefore, there is a general need for simple, high-throughput screening strategies for measuring activities in the presence and absence of inhibitors. The present invention addresses this need.

Literature

Armstrong et al. (2000) *Curr. Opin. Drug Disc. Dev.* 3:502–515; Sueyoshi et al. (1998) *FEBS Lett.* 433:211–214; Cook et al. (2000) *J. Am. Chem. Soc.* 122:8612–8622; Hemmerich and Rosen (2000) *Glycobiol.* 10:849–856; Sugahara et al. (1987) *Anal. Biochem.* 166:404–412; Mandon et al. (1994) *J. Biol. Chem.* 269:11729–11733; Hooper et al. (1993) *Anal. Biochem.* 212:128–133; Kehoe et al. (2002) *Bioorg. Med. Chem. Lett.* 12:329–332; Burkart and Wong (1999) *Anal. Biochem.* 274:131–137.

SUMMARY OF THE INVENTION

The instant invention provides methods for identifying agents that modulate an enzymatic activity of a carbohydrate sulfotransferase. The methods generally involve contacting the sulfotransferase, in a reaction solution, with a sulfate donor, a test agent, and a polymeric sulfate acceptor that is readily separated from the reaction solution. Determination of an effect of the test agent on the sulfotransferase is by detecting the amount of sulfate in the polymeric sulfate acceptor that has been separated from the reaction solution. The invention further provides kits for use in carrying out the subject methods.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a sulfotransferase" includes a plurality of such sulftotransferases and reference to "the polymeric sulfate acceptor" includes reference to one or more polymeric sulfate acceptors and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of identifying agents that modulate the activity of a carbohydrate sulfotransferase, and kits for use in performing the instant methods. The methods of the instant invention are advantageous over previously available methods of identifying agents that affect an enzymatic activity of a sulfotransferase in that the labeled product of sulfotransferase activity is readily removed from the reaction solution, e.g. is captured on a membrane or is rendered insoluble by changing the physicochemical properties of the solution, allowing for direct detection of the labeled product, and obviating the need for excessive washing and elution steps.

The methods of the invention are useful for identifying agents that modulate the enzymatic activity of a carbohydrate sulfotransferase. Agents identified using the instant methods include agents that inhibit a carbohydrate sulfotransferase activity. Where the sulfotransferase is a sulfotransferase from a pathogenic organism, such agents are useful for inhibiting a sulfotransferase activity of a pathogenic organism, and are expected to be useful for reducing viability and/or virulence of the pathogenic organism. Where the sulfotransferase is a mammalian sulfotransferase, such agents are useful for inhibiting a sulfotransferase activity of the mammal, and in some cases are expected to be useful for reducing inflammation in the mammal.

Screening Methods

The present invention provides methods of identifying agents that modulate the activity of a sulftotransferase. The methods generally involve contacting the sulfotransferase with a sulfate donor in a reaction solution that includes a detectably labeled sulfate, a test agent, and a polymeric sulfate acceptor that is readily separated from the reaction solution. After a suitable period of time, the polymeric sulfate acceptor is rendered insoluble, either by binding the polymeric sulfate acceptor to a support for which it has affinity, or by changing the physicochemical properties of the reaction solution such that the polymeric sulfate acceptor is no longer soluble in the reaction solution. The effect, if any, of the test agent on the enzymatic activity of the sulfotransferase is determined by measuring the amount of detectably labeled sulfate incorporated into the insoluble sulfate acceptor.

Assay methods of the invention may be qualitative or quantitative. Thus, as used herein, the terms "detection," "determination," and the like, refer to both qualitative and quantitative determinations, and include "measuring."

A variety of other reagents may be included in the screening assay. These include reagents like salts, neutral proteins, e.g. albumin, detergents, etc. that are used to facilitate optimal binding and/or reduce non-specific or background interactions. Reagents that improve the efficiency of the assay, such as protease inhibitors, nuclease inhibitors, anti-microbial agents, etc. may be used.

The instant screening methods may be designed a number of different ways. For example, the assay components of the method may be combined at substantially the same time or at different times. Incubations (e.g., contacting the sulfotransferase with the sulfate donor and the sulfate acceptor in a reaction solution) are performed at any suitable temperature, typically between 4° and 40° C. Incubation periods (e.g., contacting the sulfotransferase with the sulfate donor and the sulfate acceptor in a reaction solution) are selected for optimum activity, but may also be optimized to facilitate rapid high-throughput screening. The sulfotransferase is contacted with the sulfate donor and the polymeric sulfate acceptor in solution, e.g., all components are in solution. After a suitable period of time, the polymeric sulfate acceptor is rendered insoluble.

Suitable reaction times are between 0.01 and 1 hour, e.g., from about 30 seconds to about 60 seconds, from about 60 seconds to about 2 minutes, from about 2 minutes to about 5 minutes, from about 5 minutes to about 10 minutes, from about 10 minutes to about 20 minutes, from about 20 minutes to about 40 minutes, or from about 40 minutes to about 60 minutes.

Following the contact/incubation steps, the subject methods will generally, though not necessarily, further include a washing step to remove unbound components, where such a washing step is generally employed when required to remove label that would give rise to a background signal during detection, such as radioactive non-specifically bound components. Following the optional washing step, the amount of incorporated sulfate immobilized on (e.g., bound to) the support is then detected.

An "agent that modulates a sulfotransferase activity", as used herein, describes any molecule, e.g. synthetic, semi-synthetic, or natural organic or inorganic compound, protein or pharmaceutical, with the capability of altering a sulfotransferase activity of a sulfotransferase polypeptide, as described herein. Generally a plurality of assays is run in parallel with different test agent concentrations to obtain a differential response to the various concentrations. Typically, one of these concentrations serves as a negative control, i.e. at zero concentration or below the level of detection. Thus, a "suitable control" is an assay in which the sulfotransferase is contacted with the sulfate donor and the polymeric sulfate acceptor in the absence of test agent.

Sulfotransferases

Any known sulfotransferase can be used in an assay method of the invention. In many embodiments, the sulfotransferase is a carbohydrate sulfotransferase, e.g., the natural substrate for the sulfotransferase is a carbohydrate or a macromolecule comprising a carbohydrate moiety. Carbohydrate sulfotransferases that can be used in the instant invention include, but are not limited to, chondroitin 6-sulfotransferase (C6ST); chondroitin 6-sulfotransferase-2 (C6ST-2); chondroitin 4-sulfotransferase (C4ST); chondroitin 4-sulfotransferase-2 (C4ST-2); GalNAc 4-O-sulfotransferase (GalNAc4ST); GalNAc (4SO$_4$)6-O-sulfotransferase (GalNAc4S-6ST); uronosyl 2-O-sulfotransferase (UA2OST); kearatan sulfate Gal-6-sulfotransferase (KSGal6ST); GlcNAc 6-O-sulfotransferase (GalNAc6ST); high endothelial venule (HEC)-GlcNAc 6-O-sulfotransferase (HEC-GlcNAc6ST; LSST; GST-3); I-GlcNAc 6-O-sulfotransferase (I-GlcNAc6ST); GlcNA 6-O-sulfotransferase-4 (GlcNAc6ST 4); C-GlcNAc 6-O-sulfotransferase (C-GlcNAc6ST); N-deacetylase/N-sulfotransferase-1 (NDST-1); N-deacetylase/N-sulfotransferase-2 (NDST-2); N-deacetylase/N-sulfotransferase-3 (NDST-3); N-deacetylase/N-sulfotransferase-4 (NDST-4); heparan sulfate 6-sulfotransferase-1 (HS6ST-1); heparan sulfate 6-sulfotransferase-2 (HS6ST-2); heparan sulfate 6-sulfotransferase-3 (HS6ST-3); glucosaminyl 3-O-sulfotransferase-1 (3-O-ST-1); glucosaminyl 3-O-sulfotransferase-2 (3-O-ST-2); glucosaminyl 3-O-sulfotransferase-3A (3-O-ST-3A); glucosaminyl 3-O-sulfotransferase-3B (3-O-ST-3B); heparan sulfate 2-sulfotransferase (HS2ST); and Stf1–10.

The carbohydrate sulfotransferase can be from any source, including, but not limited to, a mammal (e.g., humans, felines, canines, bovines, equines, porcines, rodents, and the like); an insect; a yeast; a mold; a fungus; a bacterium (e.g., a mycobacterium); and a protozoan. In some embodiments, the carbohydrate sulfotransferase is from a pathogenic organism. Pathogenic organisms include, but are not limited to, pathogenic bacteria, pathogenic yeast, and pathogenic protozoa.

Pathogenic bacteria include, but are not limited to, *Helicobacter pyloris, Borelia burgdorferi, Legionella pneumophila*, Mycobacteria sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A Streptococcus), *Streptococcus agalactiae* (Group B Streptococcus), Streptococcus (viridans group), *Streptococcus faecalis, Streptococcus bovis*, Streptococcus (anaerobic sps.), *Streptococcus pneumoniae*, pathogenic Campylobacter sp., Enterococcus sp., *Haemophilus influenzae, Bacillus anthracis, Corynebacterium diphtheriae*, Corynebacterium sp., *Clostridium perfringens, Clostridium tetani, Enterobacter aerogenes, Klebsiella pneumoniae, Pasturella multocida*, Bacteroides sp., *Fusobacterium nucleatum*, pathogenic strains of *Escherichia coli, Streptobacillus moniliformis, Treponema pallidium, Treponema pertenue*, Leptospira, and *Actinomyces israelli*.

Infectious fungi include, but are not limited to, *Cryptococcus neoformans, Histoplasma capsulatum, Coccidioides immitis, Blastomyces dermatitidis, Chlamydia trachomatis, Candida albicans*.

Infectious protozoa include, but are not limited to, Plasmodium spp., e.g., *Plasmodium falciparum*; Trypanosomes, e.g., *Trypanosoma cruzi*; and *Toxoplasma gondii*.

Sulfate Donors

Any known sulfate donor can be used in an assay method of the invention. In many embodiments, the sulfate donor is 3'-phosphoadenosine 5'-phosphosulfate (PAPS).

The sulfate donor comprises a detectably labeled sulfate which is transferred by the sulfotransferase to the sulfate acceptor. In many embodiments, the sulfate is radioactive, i.e., $^{35}S$. In other embodiments, the sulfate is detectably labeled with a detectably labeled antibody that binds sulfate specifically.

Polymeric Sulfate Acceptors

Sulfate acceptors that are suitable for use in the methods of the instant invention are polymeric. Polymeric sulfate acceptors that are suitable for use comprise at least one moiety that is a substrate for the sulfotransferase (i.e., accepts a sulfate group transferred by the sulfotransferase), e.g., a "sulfate acceptor moiety," and further comprise a polymeric moiety. In some embodiments, the sulfate acceptor moiety is also a polymeric moiety. In other embodiments, the sulfate acceptor moiety is not a polymeric moiety, but is linked, directly or indirectly, to a polymeric moiety.

Polymeric sulfate acceptors comprise a polymeric moiety that comprises from about six to about 10, from about 10 to about 16, from about 16 to about 20, from about 20 to about 30, from about 30 to about 40, from about 40 to about 50, or more, monomer or dimer units. In some embodiments, the polymer is a homopolymer (e.g., all monomer units are identical). In other embodiments, the polymer is a heteropolymer (e.g., all monomoer units are not identical). Polymers include polyanions, polycations, hydrophobic polymers, and hydrophilic polymers. Suitable polymers include, but are not limited to, polysaccharides, polyamino acids, polyacrylamide; heparin; polypeptides, polynucleotides; polyacrylates, polyethylenes, and polyurethanes.

The polymeric sulfate acceptor is readily separated from the reaction solution by rendering it insoluble. In some embodiments, the polymeric sulfate acceptor is immobilized on a support. In these embodiments, the polymeric sulfate acceptor has affinity for the support. In other embodiments, the polymeric sulfate acceptor can be rendered insoluble by changing the physicochemical properties of the reaction solution such that the polymeric sulfate acceptor is no longer soluble in the reaction solution. The polymeric sulfate acceptor is immobilized on a support, e.g., is bound to, or associated with, the support, either covalently or non-covalently, usually non-covalently.

Immobilization on Support

In some embodiments, the polymeric sulfate acceptor is captured by the support, e.g., has affinity for a support (e.g., is bound covalently or non-covalently with the support). The support can be a wide variety of materials, and may be solid, or semi-solid, porous or non-porous. The support can be provided in a wide variety of configurations. Exemplary, non-limiting supports are described in more detail below.

In some embodiments, the sulfate acceptor moiety is also a moiety that has affinity for a support. In other embodiments, the sulfate acceptor moiety and the moiety having affinity for the support ("the capture moiety") are different.

In some embodiments, the sulfate acceptor comprises a plurality of moieties that have affinity for a support. The sulfate acceptor comprises a polymer, which polymer comprises at least one monomer that has affinity for a support. In some embodiments, the polymer is a homopolymer. In other embodiments, the polymer is a heteropolymer. In some embodiments, the repeat unit is a monomer, e.g., a monosaccharide. In other embodiments, the repeat unit is a dimer, e.g., a disaccharide.

Suitable moieties having affinity for a support ("support affinity moiety" or "affinity moiety") include, but are not limited to, carbohydrate moieties, nucleic acid moieties, peptide moieties, and lipid moieties. In some embodiments, the portion of the sulfate acceptor molecule that has affinity for a support is a polymer, e.g., a polysaccharide, a polynucleotide, a polypeptide, and the like. In some embodiments, the polymer is a homopolymer. In other embodiments, the polymer is a heteropolymer. Non-limiting examples of suitable affinity moieties include polyacrylamide; heparin; polyamino acids; polypeptides, polynucleotides; polysaccharides; polyacrylates, polyethylenes, and polyurethanes.

Suitable sulfate acceptor moieties include naturally-occurring sulfate acceptor moieties and synthetic sulfate acceptor moieties. Suitable sulfate acceptor moieties include, but are not limited to, N-acetyl galactosamine (GalNAc); glucuronic acid (GlcA); iduronic acid (IdoA); glucosamine (GlcN); GlcNAc (N-acetyl glucosamine); galactose (Gal); N-sulfated glucosamine (GlcNS); Fucose (Fuc), Glucose (Glc), and the like.

Non-limiting specific examples of sulfate acceptor molecules include, but are not limited to, a glycopeptidolipid (GPL), including, but not limited to, a GPL containing a 3,4,-di-O-methylrhamnose, and a GPL containing a 6-deoxy-talose; trehalose-containing glycolipids.

Methods for synthesizing a sulfate acceptor having affinity for a support are known in the art, and any known method can be used. An example can be found in Bovin, J. V. *Glycoconjugate J*. 15, 431–446(1998).

Supports

The support provides for mobilization of the polymeric sulfate acceptor in such a way that individual assays are distinguishable from one another, e.g., are spatially separate from one another. Any of a variety of supports can be used in the methods of the present invention. Where the support is a solid support, solid supports include, but are not limited to, beads; pins; and membranes of any shape and size. Supports comprise a variety of materials, including, but not limited to, glass, activated glass, polystyrene, polyvinyl chloride, polypropylene, poly(methyl methyacrylate), poly(dimethyl siloxane), polyethylene, polycarbonate, dextran, nylon, amyloses, natural and modified celluloses, polyacrylamides, agaroses, gels, and magnetite. The support can be functionalized to include groups that provide for binding to an affinity moiety. The support can be porous or non-porous.

The support material may have virtually any possible structural configuration so long as the polymeric sulfate acceptor is capable of being immobilized thereon, and individual assays can be spatially distinct. Thus, the support configuration may be spherical, as in a bead; cylindrical, as in the inside surface of a test tube, or the external surface of a rod; the surface may be flat such as a sheet, test strip, etc. In some embodiments, the support is a membrane.

Suitable membranes include, but are not limited to, polyvinylidene fluoride (PVDF) membranes; nitrocellulose membranes; nylon membranes, e.g., charged nylon membranes; PEI cellulose membranes, anionic cellulose membranes, charged or hydrophobic polyacrylamide or polyurethane membranes, and filter papers, e.g., Whatman paper.

Membranes that are inherently hydrophilic, or partially hydrophilic, and contain moieties appropriate for making these bonds are suitable for use with polymeric sulfate acceptors containing hydrophobic affinity moieties. Such membranes include polyamides, such as nylon, and cellulosic materials, such as cellulose, regenerated cellulose, cellulose acetate, and nitrocellulose. If the membrane used does not contain groups for binding to a polymeric sulfate acceptor affinity moiety it may be modified or derivatized appropriately.

Composite membranes are also suitable. A composite membrane comprises a porous polymer membrane substrate and an insoluble, cross-linked coating deposited thereon. Representative suitable polymers forming the membrane substrate include fluorinated polymers including poly(tetrafluoroethylene) ("TEFLON"), polyvinylidene fluoride (PVDF), and the like; polyolefins such as polyethylene, ultra-high molecular weight polyethylene (UPE), polypropylene, polymethylpentene, and the like; polystyrene or substituted polystyrenes; polysulfones such as polysulfone, polyethersulfone, and the like; polyesters including polyethylene terephthalate, polybutylene terephthalate, and the like; polyacrylates and polycarbonates; and vinyl polymers such as polyvinyl chloride and polyacrylonitriles. Copolymers can also be used for forming the polymer membrane substrate, such as copolymers of butadiene and styrene, fluorinated ethylene-propylene copolymer, ethylene-chlorotrifluoroethylene copolymer, and the like.

Generally, the support material is chosen such that a support affinity moiety has affinity for such material. A cationic support is used where the affinity moiety is an anion. For example, a nitrocellulose membrane can be used where the affinity moiety is an anion, such as a polyanion (e.g., a polynucleotide). An anionic support is used where the affinity moiety is a cation. A hydrophobic support is used where the affinity moiety is hydrophilic. For example, PVDF is a hydrophobic membrane. Polyacrylamide or other similar polymers (e.g., proteins) binds to hydrophobic membranes and thus are suitable affinity moieties.

The support can also be functionalized to have bound thereto a member of a specific binding pair, where the other member of the specific binding pair is attached to the sulfate acceptor moiety. Suitable specific binding pairs include, but are not limited to, streptavidin (detected, e.g., using labeled biotin); avidin (e.g., streptavidin) (for binding to a biotinylated biomolecule); an antigen-binding polypeptide, e.g., an immunoglobulin (Ig) or epitope-binding fragment thereof (for binding to a biomolecule comprising an epitope recognized by the Ig); polynucleotide binding proteins (for binding to a polynucleotide), e.g., a transcription factor, a translation factor, and the like; receptor-ligand systems, or other specific protein-protein interacting pairs; glycoproteins (for binding lectins); lipid-binding proteins (for binding to lipids and phospholipids), e.g., phosphatidyl serine and annexin V.

Changing Physicochemical Properties of the Reaction Solution

In some embodiments, the polymeric sulfate acceptor is rendered insoluble, and thus readily separated from the reaction solution, by changing the physicochemical properties of the reaction solution. Physicochemical properties that can be changed to render the polymeric sulfate acceptor insoluble include pH; salt concentration; temperature; polarity; and the like. For example, where the reaction is carried out a neutral pH, after a suitable reaction time, the pH can be altered so that it is acidic, such that the polymeric sulfate acceptor precipitates from the reaction solution. As another non-limiting example, after a suitable reaction time, the salt concentration of the reaction solution can be increased by adding a salt, such that the polymeric sulfate acceptor precipitates from the reaction solution. Changes in solvent polarity can also induce the polymeric substrate to precipitate. Examples of polymers that become insoluble during certain environmental changes are as follows. Charged polymers that are highly water-soluble will precipitate when organic solvents are added to the solution. Certain polyacrylamides (such as polyisopropylacrylamide-based copolymers) precipitate upon heating.

Test Agents

A variety of different candidate agents ("test agents") may be screened by the screening methods of the invention. Candidate agents encompass numerous chemical classes, though typically they are organic molecules, and may be small organic compounds having a molecular weight of more than 50 and less than about 2,500 daltons. Candidate agents may comprise functional groups necessary for structural interaction with proteins, e.g., hydrogen bonding, and can include at least an amine, carbonyl, hydroxyl or carboxyl group, or at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents, also referred to herein as "test agents") are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Separation

As noted above, after a suitable period of time, the polymeric sulfate acceptor is separated from the reaction solution, either by binding to a support (discussed below), or by changing the reaction solution properties such that the polymeric sulfate acceptor is no longer soluble in the reaction solution. As used herein, the term "separated" refers to insolubilization of the polymeric sulfate acceptor such that a partial or complete separation from the reaction solution is effected.

In some embodiments, where the polymeric sulfate acceptor is insolubilized by changing a property of the reaction solution, the polymeric sulfate acceptor forms a precipitate, and any labeled sulfate incorporated into the sulfate acceptor is detected in the precipitate. In some embodiments, the precipitate is washed to remove any $^{35}S$ that is not specifically bound to (e.g., incorporated into) the sulfate acceptor. Washing the precipitate can be performed using standard wash buffers, which generally include a salt in a concentration range of from about 1 mM to about 100 mM, a pH in the range of from about 4.0 to 8.0. Washing is generally performed at a temperature of from about 17° C. to about 40° C.

Transfer

Where the polymeric sulfate acceptor is rendered insoluble by binding to a support, after a suitable period of time, the sulfate acceptor is transferred to a support. Transfer can be accomplished by any means. For example, where the support is an array of pins, the pins can be dipped into a corresponding array of reaction mixtures.

In some embodiments, the sulfate acceptor is transferred to the support by applying a vacuum to one side of the membrane, and applying a reaction mixture to the other side such that the reaction mixture comes into contact with the membrane. The solid support affinity moiety then binds to the membrane.

In some embodiments, the support is washed to remove any $^{35}S$ that is not specifically bound to (e.g., incorporated into) the sulfate acceptor. Washing the support can be performed using standard wash buffers, which generally include a salt in a concentration range of from about 1 mM to about 100 mM, a pH in the range of from about 4.0 to 8.0. Washing is generally performed at a temperature of from about 17° C. to about 40° C.

Detection

Where the detectably labeled sulfate which is transferred by the sulfotransferase from the sulfate donor to the sulfate acceptor is detected after the sulfate acceptor is transferred to the support, the label is detected directly on the support. Where the detectably labeled sulfate which is transferred by the sulfotransferase from the sulfate donor to the sulfate acceptor is detected after the sulfate acceptor is rendered insoluble in the reaction solution by changing the solution conditions, the label is detected in the insolubilized sulfate acceptor. Detection is generally performed using instrumentation that detects $^{35}S$. For example, a phosphorimager is used to detect $^{35}S$ incorporated into the sulfate acceptor, which acceptor is immobilized on the support.

Where the sulfate acceptor is separated from the reaction solution by changing the reaction conditions, the labeled sulfate incorporated into the insolubilized sulfate acceptor is detected by standard detection means, e.g., using instrumentation that detects $^{35}S$.

Where the sulfate is detected using an antibody specific for the sulfate moiety, the antibody is generally detectably labeled, or the primary antibody is detected using a secondary antibody that is detectably labeled. Detectable labels include radioisotopes; enzymes whose products are detectable (e.g., luciferase, β-galactosidase, and the like); fluorescent labels (e.g., fluorescein isothiocyanate, rhodamine, phycoerythrin, and the like); fluorescence emitting metals, e.g., $^{152}Eu$, or others of the lanthanide series, attached to the target through metal chelating groups such as EDTA; chemiluminescent compounds, e.g., luminol, isoluminol, acridinium salts, and the like; fluorescent proteins (e.g., Anthozoa-derived fluorescent proteins, and derivatives thereof); bioluminescent compounds, e.g., luciferin, aequorin (green fluorescent protein), and the like.

Kits

The invention further provides kits for carrying out the instant methods. A subject kit generally includes a radiolabeled sulfate donor; a sulfate acceptor having affinity for a support; and a support.

The kit may optionally provide additional components that are useful in the procedure, including, but not limited to, buffers, such as wash buffers, a means for detection, control samples, standards, instructions, and interpretive information.

The invention further provides a system for performing the instant methods, the system comprising a kit of the invention, and equipment for using the kit. Exemplary equipment includes, but is not limited to, a phosphorimager, a vacuum manifold, and the like.

Finally, in many embodiments of the subject kits, the kits will further include instructions for practicing the subject methods or means for obtaining the same (e.g., a website URL directing the user to a webpage which provides the instructions), where these instructions are typically printed on a substrate, which substrate may be one or more of: a package insert, the packaging, reagent containers and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric. Standard abbreviations are used, e.g., h, hours; min, minutes; s or sec, seconds; and the like.

Example 1
Dot-blot Assay for NDST-1 and GST-3
Materials and Methods
Materials De-N-sulfated heparin was purchased from Sigma. β-GlcNAc-PAA was purchased from Glycotech Corp. Carrier free $^{35}$S-PAPS was enzymatically synthesized as previously described (Erhardt et al. (1995) *J. Bacteriol.* 177:6237–6245) using $^{35}$S-SO$_4^{2-}$ from American Radiolabeled Chemicals. A plasmid containing the sulfotransferase domain of human NDST-1 fused to glutathione S-transferase was obtained from Dr. Masahiko Negishi (NIH). The enzyme was expressed, bound to a glutathione column (Amersham Pharmacia) for purification, and cleaved from glutathione S-transferase using thrombin as described (Sueyoshi et al. (1998) *FEBS Lett.* 433:211–214). GST-3 was obtained from baculovirus-infected insect cells as previously described (Cook et al. (2000) *J. Am. Chem. Soc.* 122:8612–8622). Hybond-N$^+$ nitrocellulose membranes and Hybond-P PVDF membranes were obtained from Amersham Pharmacia, and the "Bio-Dot" dot-blot apparatus was obtained from BioRad.

NDST-1 Reactions

For the NDST-1 assay, de-N-sulfated heparin (0.02–0.1 mg) and 0.1 μg of enzyme were added to 50 mM HEPES-NaOH (pH 7.0), 0.15 M NaCl, 0.75 mg/mL protamine, 0.4% Triton X-100, 15% glycerol in a total volume of 25 μL in a 96-well plate. Reactions were initiated with 0.15 μM $^{35}$S-labeled PAPS ("$^{35}$S-PAPS")(0.1–0.5 μCi per reaction), incubated at 25° C. for 15 min, and terminated by the addition of 30 μL of MeOH. A 15-μL aliquot was removed from each well and diluted 100-fold, and 15–25 μL were then transferred to the wells of the dot-blot apparatus. A vacuum was applied, and the wells were washed and eluted as described below. Control reactions with heat-killed (100° C., 5 min) enzyme were included to monitor background binding of $^{35}$S-PAPS and $^{35}$S-SO$_4^{2-}$ to the membrane after washing.

GST-3 Reactions

A typical assay included an appropriate volume of enzyme solution, 0.6–1.0 μg of β-GlcNAc-PAA, 0.1% Triton X-100, 10% glycerol, 4 mM Mg(OAc)$_2$, 10 mM NaF, 1 mM ATP, in 30 mM HEPES-NaOH (pH 6.0), diluted to a total volume of 25 μL in a 96-well plate. Reactions were initiated with 2.0 μM $^{35}$S-PAPS (0.1–0.5 μCi per reaction), incubated at 25° C. for 2 h, and terminated with 30 μL of MeOH. A 15-μL aliquot was removed from each well and diluted 100-fold, and 15–25 μL of the solution were transferred to the wells of the dot-blot apparatus. A vacuum was applied, and the wells were washed and eluted as described below. Control reactions with heat-killed enzyme were included to monitor background binding of $^{35}$S-PAPS and $^{35}$S-SO$_4^{2-}$ to the membrane after washing.

Isolation of $^{35}$S-Labeled Heparin and $^{35}$S-Labeled GlcNAc-PAA on Membranes Hybond-N+ membranes were pre-wetted with H$_2$O and Hybond-P membranes were pre-wetted with MeOH before assembling the dot-blot apparatus. The quenched and diluted reactions were added to the wells, and a vacuum was applied to load products onto the membrane. To elute $^{35}$S-PAPS while retaining $^{35}$S-labeled heparin or GlcNAc-PAA on the membrane, the wells were washed twice with 40 μL of PAPS elution buffer (EB) ((NH$_4$)$_2$SO$_4$ pH 3.0), while maintaining a gentle vacuum. The apparatus was disassembled, and the membrane briefly soaked (30 sec) with gentle agitation in EB (10 mL). This was repeated once more with fresh EB. The membrane was then rinsed with H$_2$O and allowed to dry. The amount of $^{35}$S-labeled product associated with the membrane was then quantified by phosphorimaging.

Validation of Substrates Using a Paper Chromatography Assay $^{35}$S-PAPS and de-N-sulfated heparin (or β-GlcNAc-PAA) were incubated with NDST-1 (or GST-3) for 1 h. The reactions were terminated with an equal volume of methanol and 5-μL aliquots were spotted onto Whatman #1 TLC paper. The paper was then eluted with 95% ethanol/1 M ammonium acetate, pH 7.8 (5:2 v/v) for 6 h, air-dried, and visualized by phosphorimaging. Using this solvent system, highly anionic $^{35}$S-labeled polymeric products remained at the origin of the paper, while $^{35}$S-PAPS and $^{35}$S—SO$_4^{2-}$ (from PAPS hydrolysis) migrated substantially. The presence of an intense spot at the origin of the test reactions with active enzymes, and the absence of this spot in the heat-killed enzyme controls, confirmed enzymatic activity with each substrate.

Results

As stated above, the carbohydrate substrates used in the assays were chosen based on issues of convenience and amenability with membrane capture. While they embody the essential recognition elements for their respective enzymes, it should be noted that the chosen substrates are not native. Therefore, we felt it necessary to validate their substrate activity independently prior to use in the dot-blot assay. This was accomplished using a TLC-based method (see Materials and Methods section).

Figures 1A, 1B:
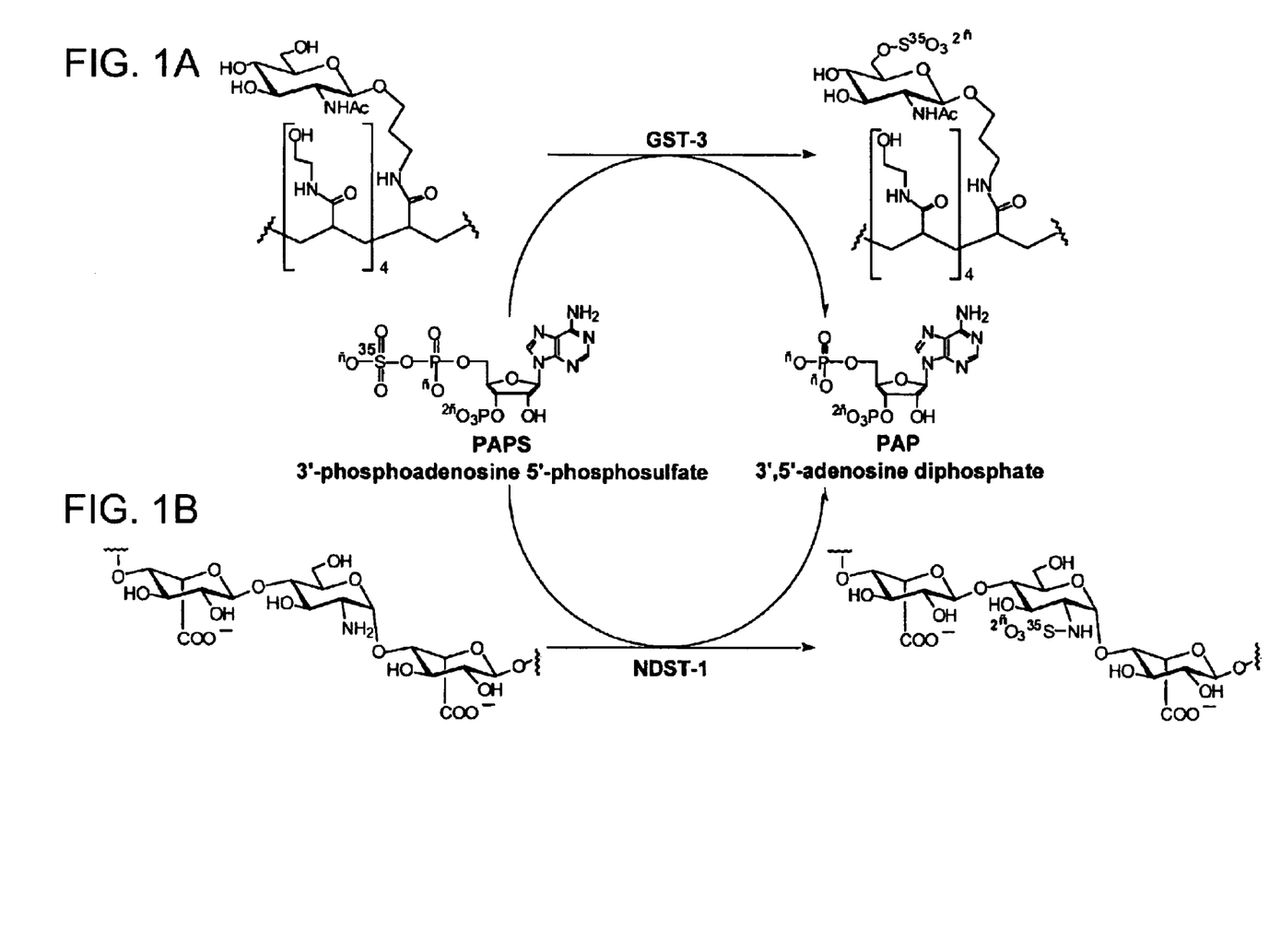
FIGS. 1A and 1B depict assays for GST-3 and NDST-1 using polymeric substrates.
Figure 2A:
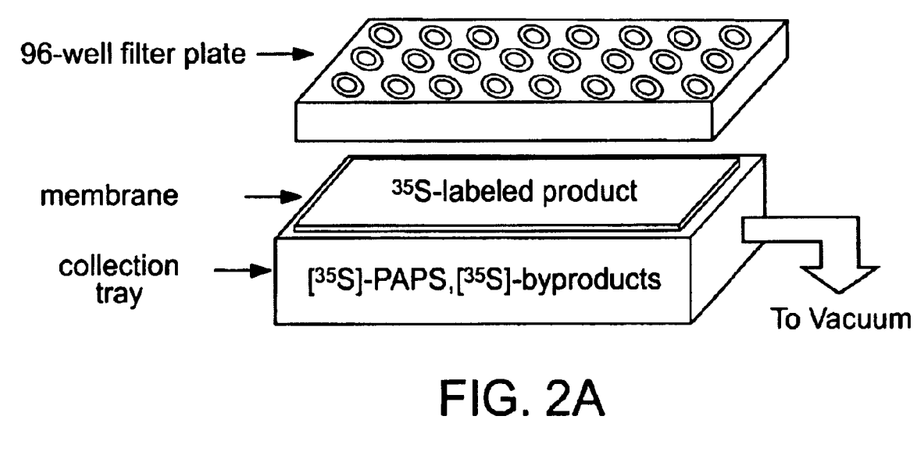
FIG. 2A is a schematic representation of a dot-blot strategy for monitoring the effect of an agent on the enzymatic activity of a sulfotransferase.
Figure 2B:
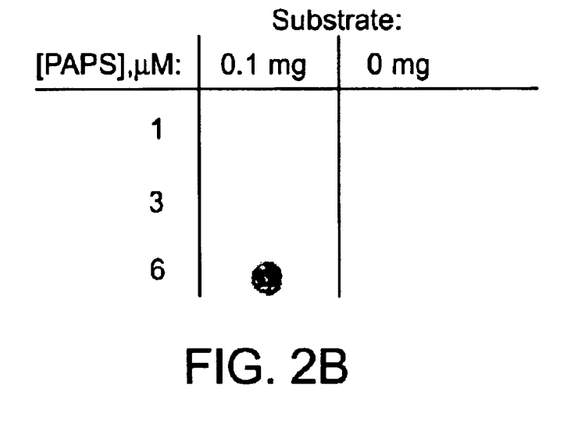
FIG. 2B is a phosphorimaged membrane showing sulfation of de-N-sulfated heparin using a screen for NDST-1 activity.

In the process of developing the dot-blot assay, the most significant challenge was to identify conditions for eluting unreacted $^{35}$S-PAPS and its hydrolysis products from the membrane, while still retaining $^{35}$S-labeled carbohydrate products. We tested a wide range of potential elution buffers at various pHs and concentrations, including Tris-HCl, SDS, NH$_4$OAc, LiCl and (NH$_4$)$_2$SO$_4$. It was found that 1.25 M (NH$_4$)$_2$SO$_4$(pH 3.0) was a reliable buffer for eliminating background binding of $^{35}$S-PAPS and its hydrolysis products (FIG. 2). It should be noted that N-sulfate esters of heparin are known to be stable to hydrolysis at this pH for incubations up to 24 hours. We therefore felt confident that the elution and washing conditions would not destroy radiolabeled product.

Figure 3A:
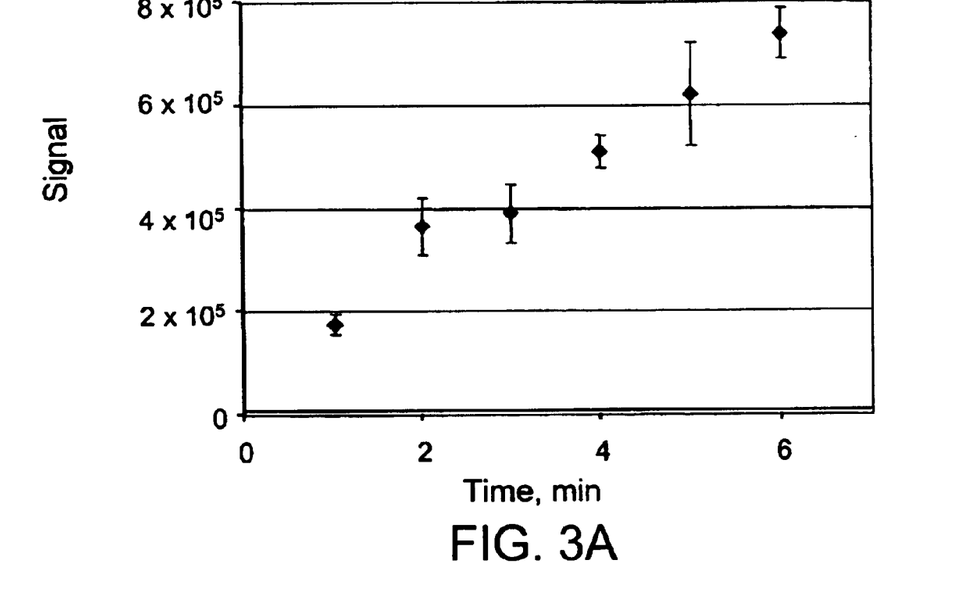
FIGS. 3A and 3B are graphs depicting time dependence of polymer sulfation for NDST-1 with 3 $\mu$M PAPS and 0.10 mg de-N-sulfated heparin (FIG. 3A) and GST-3 with 2 $\mu$M PAPS and 0.63 mg β-GlcNAc-PAA (FIG. 3B).
Figure 3B:
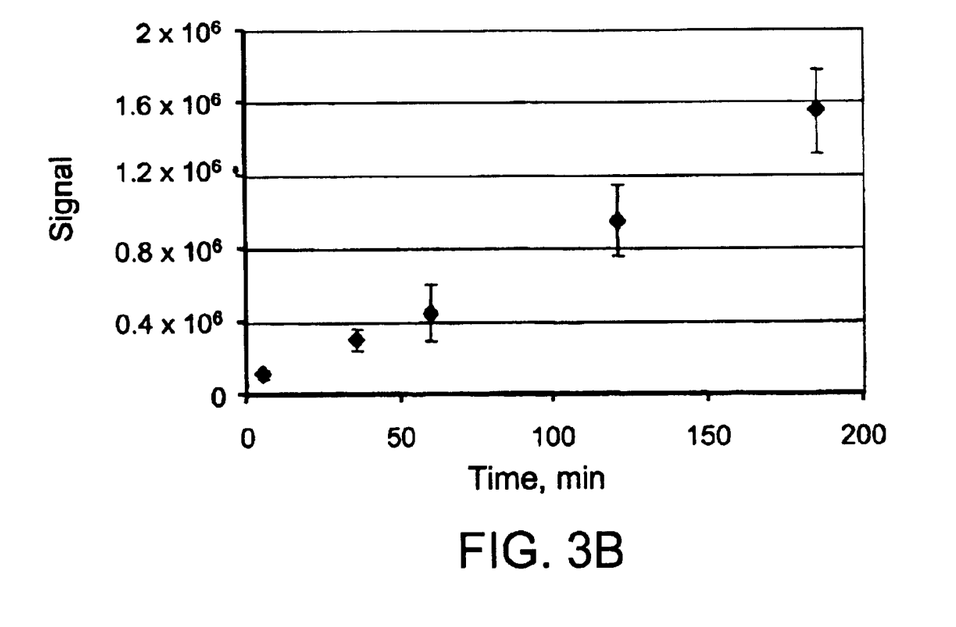
Figure 4A:
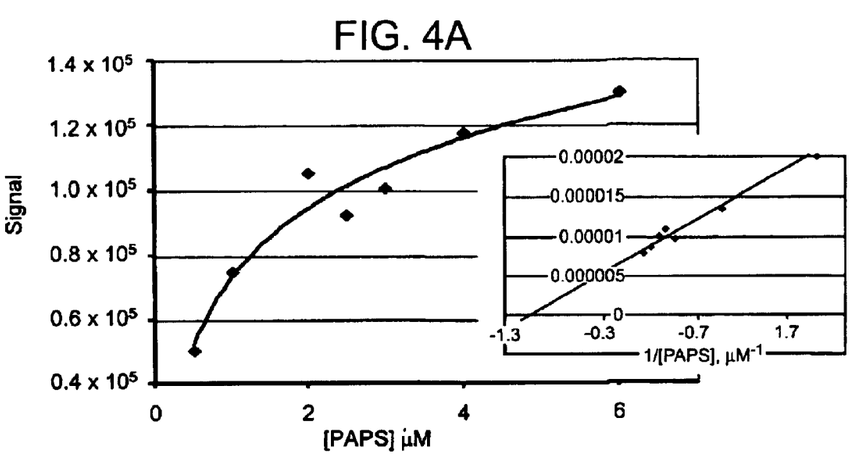
FIGS. 4A and 4B are saturation curves of phosphorimaging signal vs. concentration of PAPS, and corresponding double-reciprocal plots of rate vs. PAPS concentration for NDST-1 (FIG. 4A) and GST-3 (FIG. 4B).
Figure 4B:
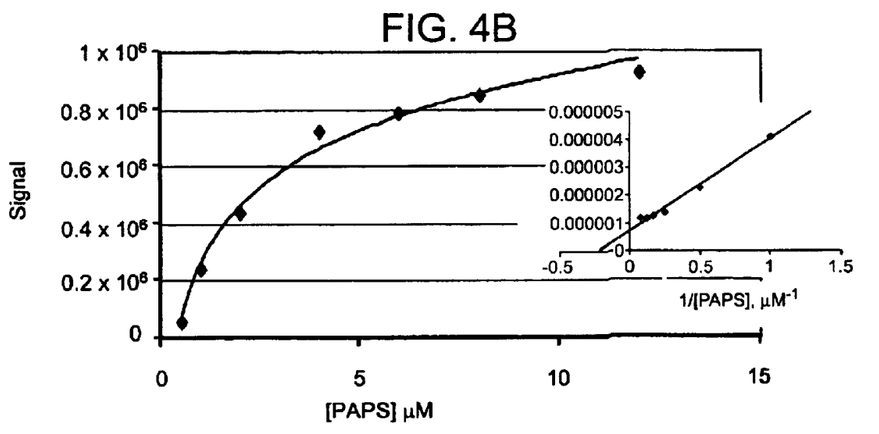

We performed initial rate studies with each enzyme to confirm a linear incorporation of $^{35}$S-sulfate into the carbohydrate substrate with respect to time (FIG. 3). Based on extensive prior characterization of NDST-1 and GST-3 with various substrates, we assumed that the products formed were sulfated exclusively at the 2-N position of glucosamine and 6-OH of GlcNAc, respectively, without further characterization (Mandon et al. (1994) *J. Biol. Chem.* 269:11729–11733; Cook et al. (2000) *J. Am. Chem. Soc.* 122:8612–8622). Next, we established that $^{35}$S-labeled product formation was also linear with respect to the amount of $^{35}$S-labeled PAPS included in the assay at low levels of conversion. K$_M$ (PAPS) values were obtained using Michaelis-Menten methods and were found to be in good agreement with published values for these enzymes (FIG. 4).

We were unable to obtain K$_M$ values for the polymeric carbohydrate substrates due to their heterogeneous nature and the presence of multiple sulfation sites on each polymer chain. However, for both enzymes product formation appeared linear within a range of polymer concentrations. At higher substrate concentrations (see the Materials and Methods section for substrate concentration ranges) a significant drop in signal was observed, obscuring further analysis. This might be attributed to membrane saturation at high concentrations of sulfated polymer. In order to circumvent the membrane capacity problem, we diluted the terminated enzyme reactions 100-fold prior to applying aliquots to the membrane. Under these conditions, product formation was found to be linear with substrate concentration.

Figure 5A:
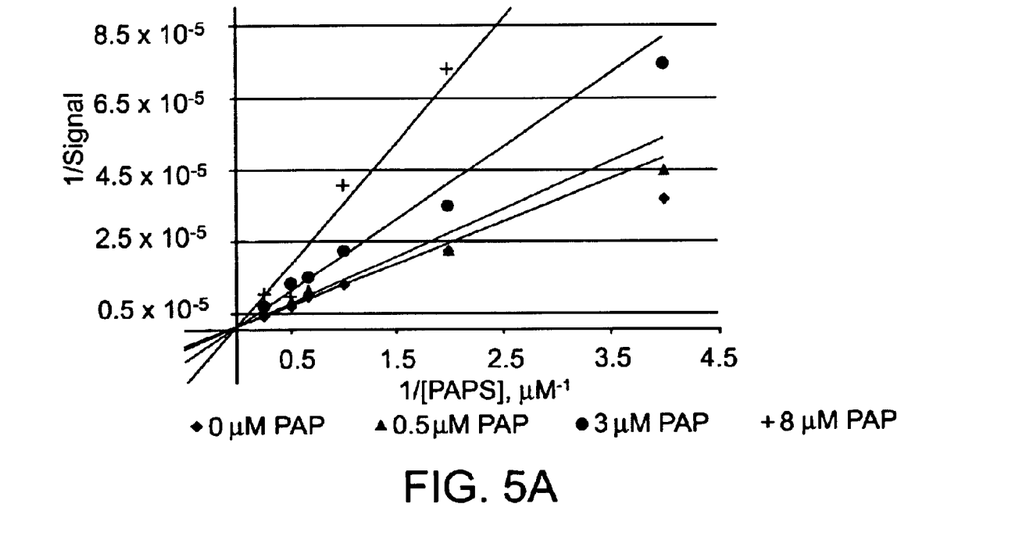
FIGS. 5A and 5B are Lineweaver-Burk plots for NDST-1 (FIG. 5A) and GST-3 (FIG. 5B).
Figure 5B:
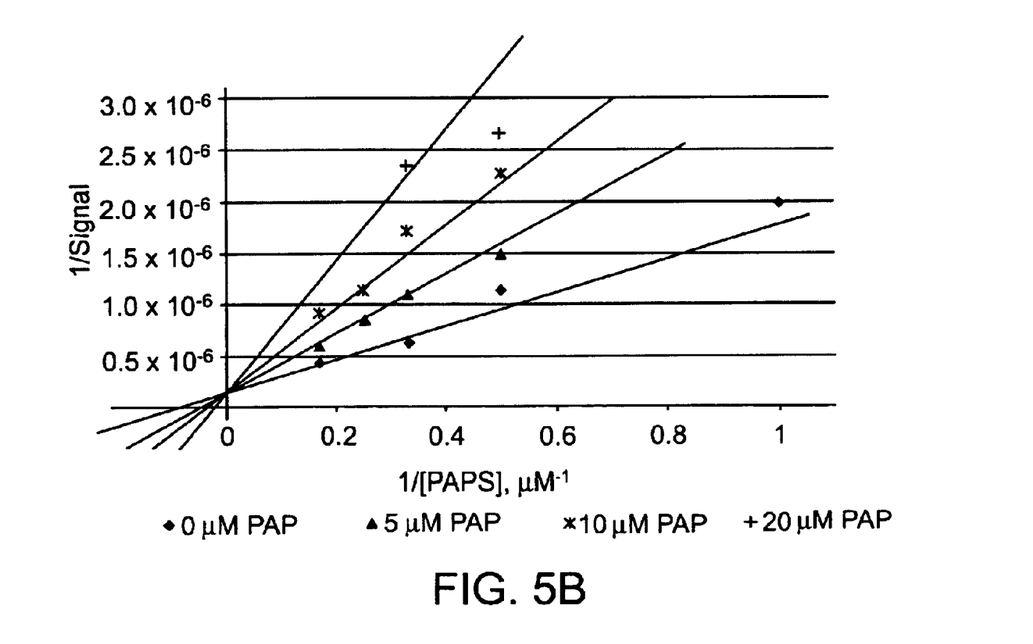

Finally, we validated the assay as a means to measure enzyme inhibition using the product of the ST reaction, 3',5'-ADP as a model inhibitor. As can be seen from double reciprocal plots of signal versus PAPS concentration, 3',5'-ADP is a competitive inhibitor (versus PAPS) for both enzymes as expected (FIG. 5).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of identifying an agent that modulates an enzymatic activity of a carbohydrate sulfotransferase, the method comprising:
    a) contacting the sulfotransferase in a reaction solution with:
        i) a sulfate donor that comprises a detectably labeled sulfate group;
        ii) a polymeric sulfate acceptor; and
        iii) a test agent;
    b) separating the polymeric sulfate acceptor from the reaction solution, wherein the polymeric sulfate acceptor comprises a hydrophilic moiety and has affinity for a hydrophobic support, and wherein the polymeric sulfate acceptor is separated from the reaction solution by binding to the hydrophobic support; and
    c) determining the effect, if any, of the test agent on the enzymatic activity of the sulfotransferase, wherein an alteration in the amount of detectably labeled sulfate group incorporated into the polymeric sulfate acceptor separated from the reaction solution, compared with a control in the absence of the test agent, indicates that the test agent modulates the enzymatic activity of the sulfotransferase.

2. The method according to claim 1, wherein support is a membrane.

3. The method according to claim 2, wherein the hydrophobic membrane is a polyvinylidene fluoride membrane.

4. The method according to claim 1, wherein the polymeric sulfate acceptor is β-GlcNAc-PAA.

5. The method according to claim 3, wherein the polymeric sulfate acceptor comprises an anionic moiety, and the support is a cationic membrane.

6. The method according to claim 5, wherein the cationic membrane is a nitrocellulose membrane.

7. The method according to claim 5, wherein the polymeric sulfate acceptor is N-desulfated heparin.

8. The method according to claim 1, wherein the sulfate donor is $^{35}$S-labeled 3'-phosphoadenosine 5'-phosphosulfate.

9. A kit for identifying an agent that modulates an enzymatic activity of a carbohydrate sulfotransferase, the kit comprising:
    an $^{35}$S-labeled sulfate donor;
    a polymeric sulfate acceptor comprising a hydrophilic moiety that has affinity for a hydrophobic support; and
    a hydrophobic support.

10. A kit for identifying an agent that modulates an enzymatic activity of a carbohydrate sulfotransferase, the kit comprising:
    an $^{35}$S-labeled sulfate donor;
    a polymeric sulfate acceptor comprising an anionic moiety that has affinity for a cationic support; and
    a cationic support.

11. A method of identifying an agent that modulates an enzymatic activity of a carbohydrate sulfotransferase, the method comprising:
    a) contacting the sulfotransferase in a reaction solution with:
        i) a sulfate donor that comprises a detectably labeled sulfate group;
        ii) a polymeric sulfate acceptor; and
        iii) a test agent;
    b) separating the polymeric sulfate acceptor from the reaction solution, wherein the polymeric sulfate acceptor comprises an anionic moiety and has affinity for a cationic support, and wherein the polymeric sulfate acceptor is separated from the reaction solution by binding to the cationic support; and
    c) determining the effect, if any, of the test agent on the enzymatic activity of the sulfotransferase, wherein an alteration in the amount of detectably labeled sulfate group incorporated into the polymeric sulfate acceptor separated from the reaction solution, compared with a control in the absence of the test agent, indicates that the test agent modulates the enzymatic activity of the sulfotransferase.

12. The method of claim 11, wherein the cationic support is a membrane.

13. The method of claim 12, wherein the membrane is a nitrocellulose membrane.

14. The method of claim 11, wherein the polymeric sulfate acceptor is N-desulfated heparin.

15. A method of identifying an agent that modulates an enzymatic activity of a carbohydrate sulfotransferase, the method comprising:
    a) contacting the sulfotransferase in a reaction solution with:
        iv) a sulfate donor that comprises a detectably labeled sulfate group;
        v) a polymeric sulfate acceptor; and
        vi) a test agent;
    b) separating the polymeric sulfate acceptor from the reaction solution by rendering the polymeric sulfate acceptor insoluble; and
    c) determining the effect, if any, of the test agent on the enzymatic activity of the sulfotransferase, wherein an alteration in the amount of detectably labeled sulfate group incorporated into the polymeric sulfate acceptor separated from the reaction solution, compared with a control in the absence of the test agent, indicates that the test agent modulates the enzymatic activity of the sulfotransferase.

16. The method according to claim 15, wherein the polymeric sulfate acceptor is separated from the reaction solution by changing the pH of the reaction solution.

17. The method according to claim 15, wherein the polymeric sulfate acceptor is separated from the reaction solution by changing the salt concentration of the reaction solution.

* * * * *